(12) United States Patent
McCoy

(10) Patent No.: US 9,101,477 B2
(45) Date of Patent: Aug. 11, 2015

(54) ANTERIOR OFFSET COMPONENT FOR TOTAL HIP REPLACEMENT

(76) Inventor: Thomas Hatton McCoy, Charlotte, NC (US)

( * ) Notice: Subject to any disclaimer, the term of this patent is extended or adjusted under 35 U.S.C. 154(b) by 0 days.

(21) Appl. No.: 13/274,844

(22) Filed: Oct. 17, 2011

(65) Prior Publication Data

US 2013/0096690 A1    Apr. 18, 2013

(51) Int. Cl.
*A61F 2/36*    (2006.01)
*A61F 2/30*    (2006.01)

(52) U.S. Cl.
CPC ....... *A61F 2/367* (2013.01); *A61F 2002/30574* (2013.01); *A61F 2002/3652* (2013.01); *A61F 2002/3684* (2013.01)

(58) Field of Classification Search
CPC .............. A61F 2/36; A61F 2002/3631; A61F 2002/3637; A61F 2002/3652; A61F 2002/3656
USPC ........................................... 623/23.15–23.35
See application file for complete search history.

(56) References Cited

U.S. PATENT DOCUMENTS

| | | | |
|---|---|---|---|
| 5,645,607 A | 7/1997 | Hickey | |
| 6,723,130 B2* | 4/2004 | Draenert et al. | 623/23.35 |
| 7,468,078 B2 | 12/2008 | Sederholm et al. | |
| 7,534,271 B2* | 5/2009 | Ries et al. | 623/23.21 |
| 7,833,277 B2 | 11/2010 | Saladino et al. | |
| 2001/0008981 A1* | 7/2001 | Masini | 623/22.42 |
| 2003/0078670 A1* | 4/2003 | Grimes | 623/23.21 |
| 2004/0107001 A1* | 6/2004 | Cheal et al. | 623/22.42 |
| 2004/0138757 A1 | 7/2004 | Nadzadi et al. | |
| 2008/0167723 A1 | 7/2008 | Acker et al. | |

(Continued)

FOREIGN PATENT DOCUMENTS

| | | |
|---|---|---|
| EP | 0485311 A1 | 5/1992 |
| FR | 2753081 A1 | 3/1998 |
| FR | 2889446 A1 | 2/2007 |

(Continued)

OTHER PUBLICATIONS

European Patent Office. PCT International Search Report and Written Opinion dated Jan. 14, 2013. International Application No. PCT/US2012/060043. International Filing Date: Oct. 12, 2012. Name of Applicant: McCoy, Thomas Hatton. English Language. 12 pages.
International Preliminary Report on Patentability and Written Opinion for International Application No. PCT/US2012/060043 dated Apr. 22, 2014.

*Primary Examiner* — Bruce E Snow
(74) *Attorney, Agent, or Firm* — Moore & Van Allen PLLC; Patrick B. Horne

(57) ABSTRACT

A component is configured for implantation during a total hip replacement procedure being performed on a patient having an anterior and posterior. The component includes a stem configured for intraosseous femoral implantation. The stem has a distal end configured for femoral insertion and a proximal end opposite the distal end. The component has a neck attached to the stem at a neck-stem junction. The neck has a proximal end proximate the neck-stem junction and a distal end opposite the proximal end. The neck is configured for extraosseous implantation. The component also has a head attached to the neck proximate the distal end of the neck. The head is configured for coupling with a ball configured for coupling with a socket implanted in an acetabulum of a pelvis of the patient during the procedure, thereby forming a total hip replacement. The head is anteriorly offset relative to the stem.

7 Claims, 18 Drawing Sheets

(56) References Cited

U.S. PATENT DOCUMENTS

2009/0326672 A1 12/2009 McCleary et al.
2010/0292806 A1 11/2010 Daniels et al.

FOREIGN PATENT DOCUMENTS

| WO | WO 0048535 A1 | 8/2000 |
| WO | WO 2009/046152 A1 | 4/2009 |

* cited by examiner

ANTERIOR OFFSET COMPONENT FOR TOTAL HIP REPLACEMENT

FIELD

In general, embodiments of the invention relate to hip replacements. More specifically, embodiments of the invention relate to femoral components of total hip replacements.

BACKGROUND

Recent years have seen drastic improvement in joint replacement technology. Specifically hip replacement technology has improved drastically. Modern total hip replacement methods involve implantation of a femoral component. The femoral component has an intraosseous stem attached to an extraosseous neck and head. The head couples with an acetabular cup or socket, thereby forming a total hip replacement. While many designs of hip replacement provide viable solutions for ailing patients, hip dislocations, both anteriorly and posteriorly, remain a common complication. Using current designs, attempts to minimize the dislocation risk, such as by anterior displacement of the head relative to the intraosseous stem, can result in other negative outcomes, specifically leg lengthening, in-toeing gait and diminution of abductor movement.

Most femoral stems are manufactured with no built-in anterior displacement of the head relative to the intraosseous stem. Those femoral stems that provide anterior displacement of the head relative to the intraosseous stem do so by angulating the prosthetic neck in the transverse plane. Such transverse plane angulation may be accomplished with modular components or it may be accomplished by angulation to a set degree in a non-modular femoral component. However, as mentioned above, such components can result in significant negative outcomes.

In some early designs, the femoral components were angulated in the sagittal plane at the level of the intraosseous stem itself. Such designs have been abandoned because having a bent intraosseous stem makes insertion of the stem less reliable and extraction more difficult.

SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

Embodiments of the invention are directed to providing anterior displacement of the head relative to the intraosseous stem, thereby minimizing instances of dislocation, while also minimizing instances of other negative outcomes. A first embodiment provides anterior displacement of the head relative to the stem by offsetting the neck and head relative to the stem proximate the junction of the stem and the neck. A second embodiment provides anterior displacement of the head relative to the stem by angulating, in the extraosseous portion of the component, the neck relative to the stem in the sagittal plane. A third embodiment provides anterior displacement of the head relative to the stem by both (1) offsetting the neck and head relative to the stem proximate the junction of the stem and the neck and (2) angulating, in the extraosseous portion of the component, the neck relative to the stem in the sagittal plane.

According to embodiments of the invention, a component is configured for implantation during a total hip replacement procedure being performed on a patient. The patient has an anterior and posterior, and the component includes a stem configured for intraosseous femoral implantation. The stem has a distal end configured for femoral insertion and a proximal end opposite the distal end. The component also has a neck attached to the stem at a neck-stem junction. The neck has a proximal end proximate the neck-stem junction and a distal end opposite the proximal end, and the neck is configured for extraosseous implantation. The component also has a head attached to the neck proximate the distal end of the neck, and the head is configured for coupling with a socket implanted in an acetabulum of a pelvis of the patient during the procedure, thereby forming a total hip replacement. The neck is anteriorly offset relative to the stem proximate the neck-stem junction, thereby anteriorly offsetting the head relative to the stem.

In some embodiments, substantially all or all of the neck is anteriorly offset with respect to the stem. In some embodiments, the neck comprises a modular neck whereby the neck is configured for reconfiguration of position relative to the stem. In some embodiments, the neck is configured for reconfiguration of angular position in the sagittal plane of the patient. In some embodiments, the proximal end of the neck and the distal end of the neck are anteriorly offset relative to the stem substantially the same amount.

According to embodiments of the invention, a component is configured for implantation during a total hip replacement procedure being performed on a patient. The patient has an anterior and posterior, and the component includes a stem configured for intraosseous femoral implantation. The stem has a distal end configured for femoral insertion and a proximal end opposite the distal end. The component also has a neck attached to the stem at a neck-stem junction. The neck has a proximal end proximate the neck-stem junction and a distal end opposite the proximal end, and the neck is configured for extraosseous implantation. The component also has a head attached to the neck proximate the distal end of the neck, and the head is configured for coupling with a socket implanted in an acetabulum of a pelvis of the patient during the procedure, thereby forming a total hip replacement. The neck is angled with respect to the stem in the sagittal plane of the patient, thereby anteriorly offsetting the head relative to the stem.

In some embodiments, the distal end of the neck is anteriorly offset relative to the stem. In some embodiments, the neck comprises a modular neck configured for reconfiguration of position relative to the stem. In some embodiments, the neck is configured for reconfiguration of angular position with respect to the stem and in the sagittal plane of the patient.

According to embodiments of the invention, a component is configured for implantation during a total hip replacement procedure being performed on a patient. The patient has an anterior and posterior, and the component includes a stem configured for intraosseous femoral implantation. The stem has a distal end configured for femoral insertion and a proximal end opposite the distal end. The component also has a neck attached to the stem at a neck-stem junction. The neck has a proximal end proximate the neck-stem junction and a distal end opposite the proximal end, and the neck is configured for extraosseous implantation. The component also has a head attached to the neck proximate the distal end of the neck, and the head is configured for coupling with a socket implanted in an acetabulum of a pelvis of the patient during the procedure, thereby forming a total hip replacement. The neck is anteriorly offset relative to the stem proximate the neck-stem junction, thereby anteriorly offsetting the head relative to the stem. Also, the neck is angled with respect to the stem in the sagittal plane of the patient, thereby further anteriorly offsetting the head relative to the stem.

In some embodiments, the neck comprises a modular neck whereby the neck is configured for reconfiguration of position relative to the stem. In some embodiments, the neck is configured for reconfiguration of angular position in the sagittal plane of the patient.

According to embodiments of the invention, a total hip replacement system for implantation during a total hip replacement procedure being performed on a patient, the patient having an anterior and posterior, includes a socket component configured for implantation in an acetabulum of a pelvis of the patient during the procedure. The system also includes a femoral component configured for implantation in a femur of the patient and configured for coupling with the socket component. The femoral component includes a stem configured for intraosseous femoral implantation. The stem has a distal end configured for femoral insertion and a proximal end opposite the distal end. The femoral component also has a neck attached to the stem at a neck-stem junction, and the neck having a proximal end proximate the neck-stem junction and a distal end opposite the proximal end. The neck is configured for extraosseous implantation. The femoral component also has a head attached to the neck proximate the distal end of the neck, and the head is configured for coupling with the socket component, thereby forming a total hip replacement. The neck is anteriorly offset relative to the stem proximate the neck-stem junction, thereby anteriorly offsetting the head relative to the stem.

In some embodiments, the neck is angled with respect to the stem in the sagittal plane of the patient, thereby further anteriorly offsetting the head relative to the stem. In some embodiments, substantially all or all of the neck is anteriorly offset with respect to the stem. In some embodiments, the neck comprises a modular neck whereby the neck is configured for reconfiguration of position relative to the stem. In some embodiments, the neck is configured for reconfiguration of angular position in the sagittal plane of the patient. In some embodiments, the proximal end of the neck and the distal end of the neck are anteriorly offset relative to the stem substantially the same amount.

According to embodiments of the invention, a total hip replacement system for implantation during a total hip replacement procedure being performed on a patient, the patient having an anterior and posterior, includes a socket component configured for implantation in an acetabulum of a pelvis of the patient during the procedure. The system also includes a femoral component configured for implantation in a femur of the patient and configured for coupling with the socket component. The femoral component includes a stem configured for intraosseous femoral implantation. The stem has a distal end configured for femoral insertion and a proximal end opposite the distal end. The femoral component also has a neck attached to the stem at a neck-stem junction, and the neck having a proximal end proximate the neck-stem junction and a distal end opposite the proximal end. The neck is configured for extraosseous implantation. The femoral component also has a head attached to the neck proximate the distal end of the neck, and the head is configured for coupling with the socket component, thereby forming a total hip replacement. The neck is anteriorly offset relative to the stem proximate the neck-stem junction, thereby anteriorly offsetting the head relative to the stem.

In some embodiments, the neck comprises a modular neck configured for reconfiguration of position relative to the stem. In some embodiments, the neck is configured for reconfiguration of angular position with respect to the stem and in the sagittal plane of the patient.

To the accomplishment of the foregoing and related ends, the one or more embodiments comprise the features hereinafter fully described and particularly pointed out in the claims. The following description and the annexed drawings set forth in detail certain illustrative features of the one or more embodiments. These features are indicative, however, of but a few of the various ways in which the principles of various embodiments may be employed, and this description is intended to include all such embodiments and their equivalents.

BRIEF DESCRIPTION OF THE DRAWINGS

Figure 1:
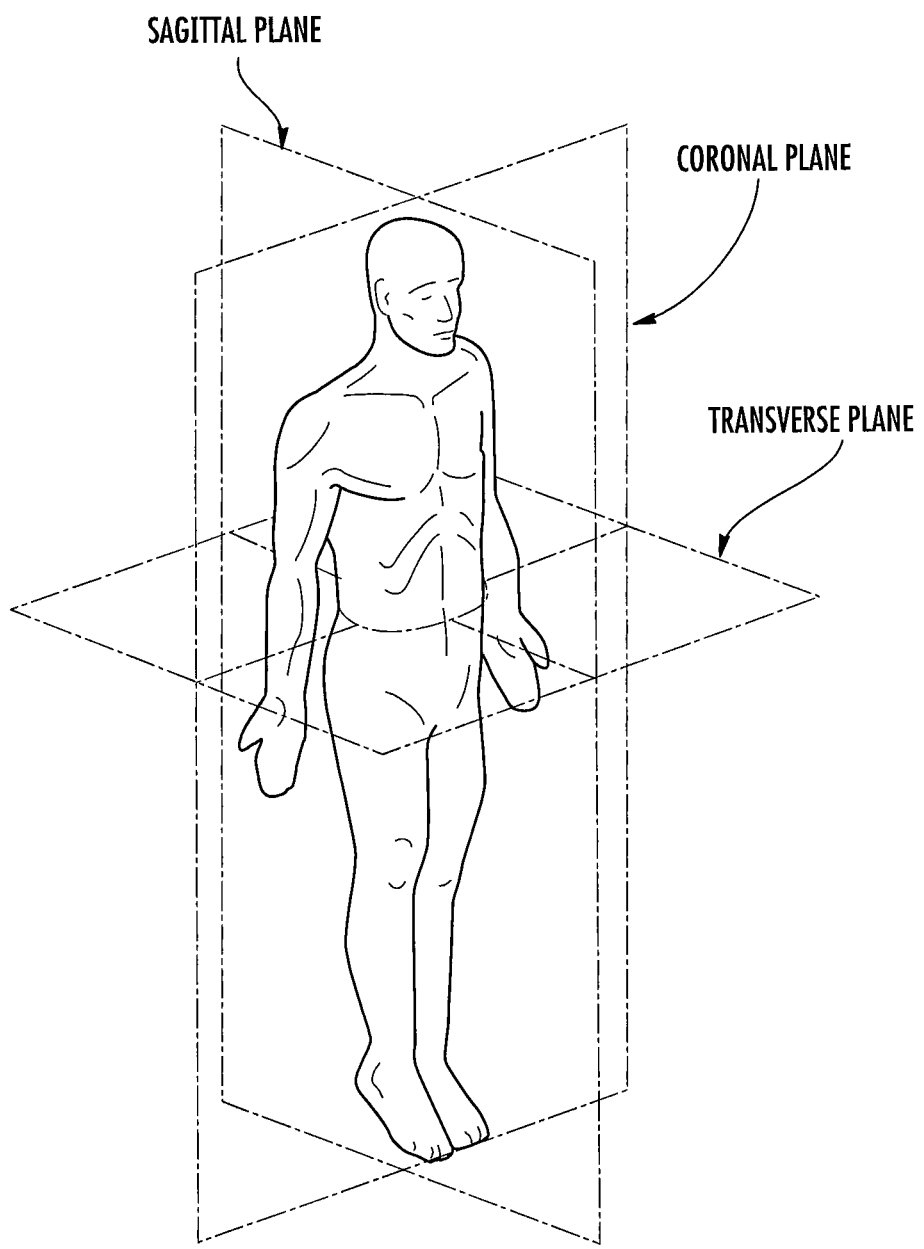
Figure 2:
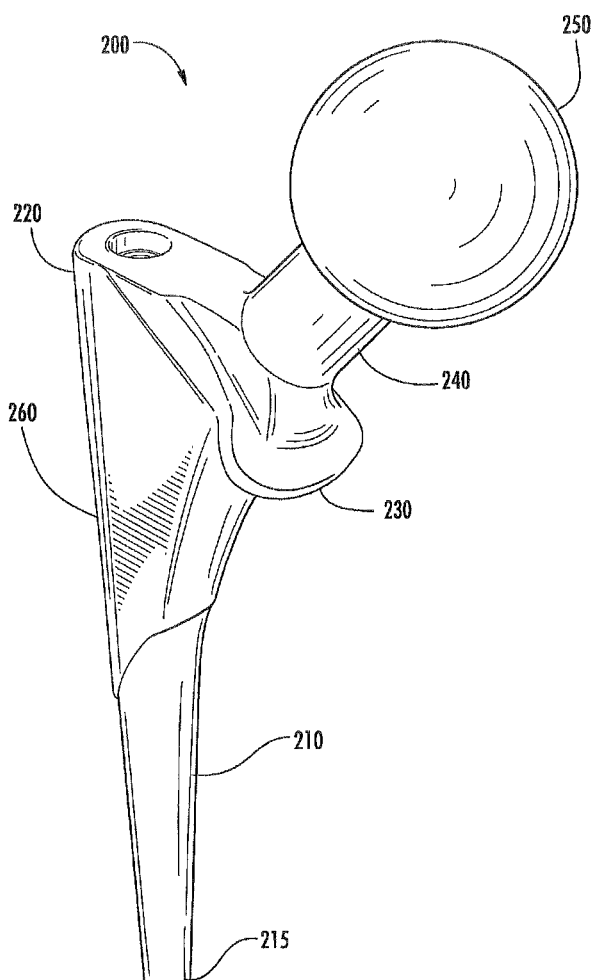
Figure 3A:
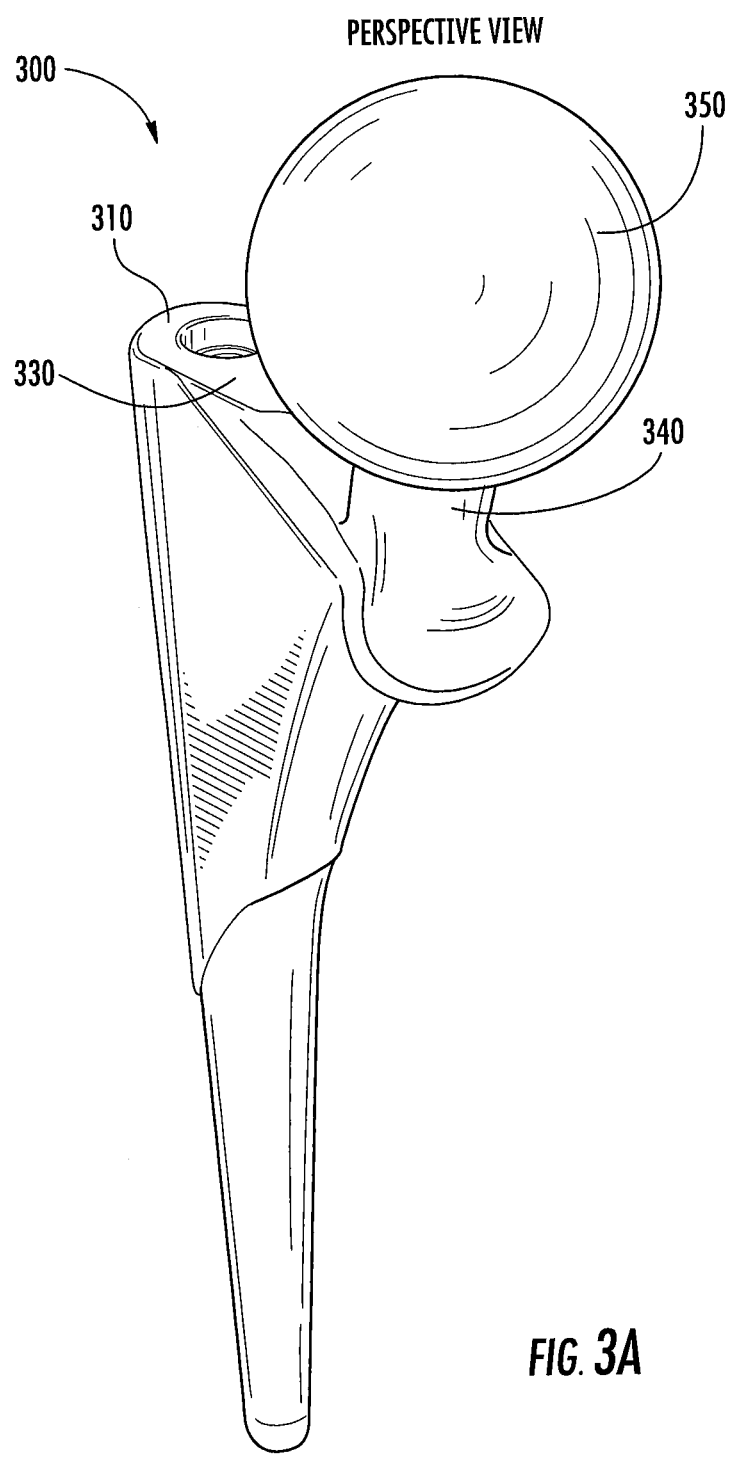

Having thus described embodiments of the invention in general terms, reference will now be made to the accompanying drawings, which are not necessarily drawn to scale, and wherein:

FIG. 1 is a reference diagram illustrating a sagittal plane, a coronal plane, and a transverse plane of a representative patient;

FIG. 2 is a diagram illustrating a femoral component for use in a hip replacement procedure;

FIG. 3A is a perspective diagram illustrating a femoral component for use in a hip replacement procedure.

Figure 3B:
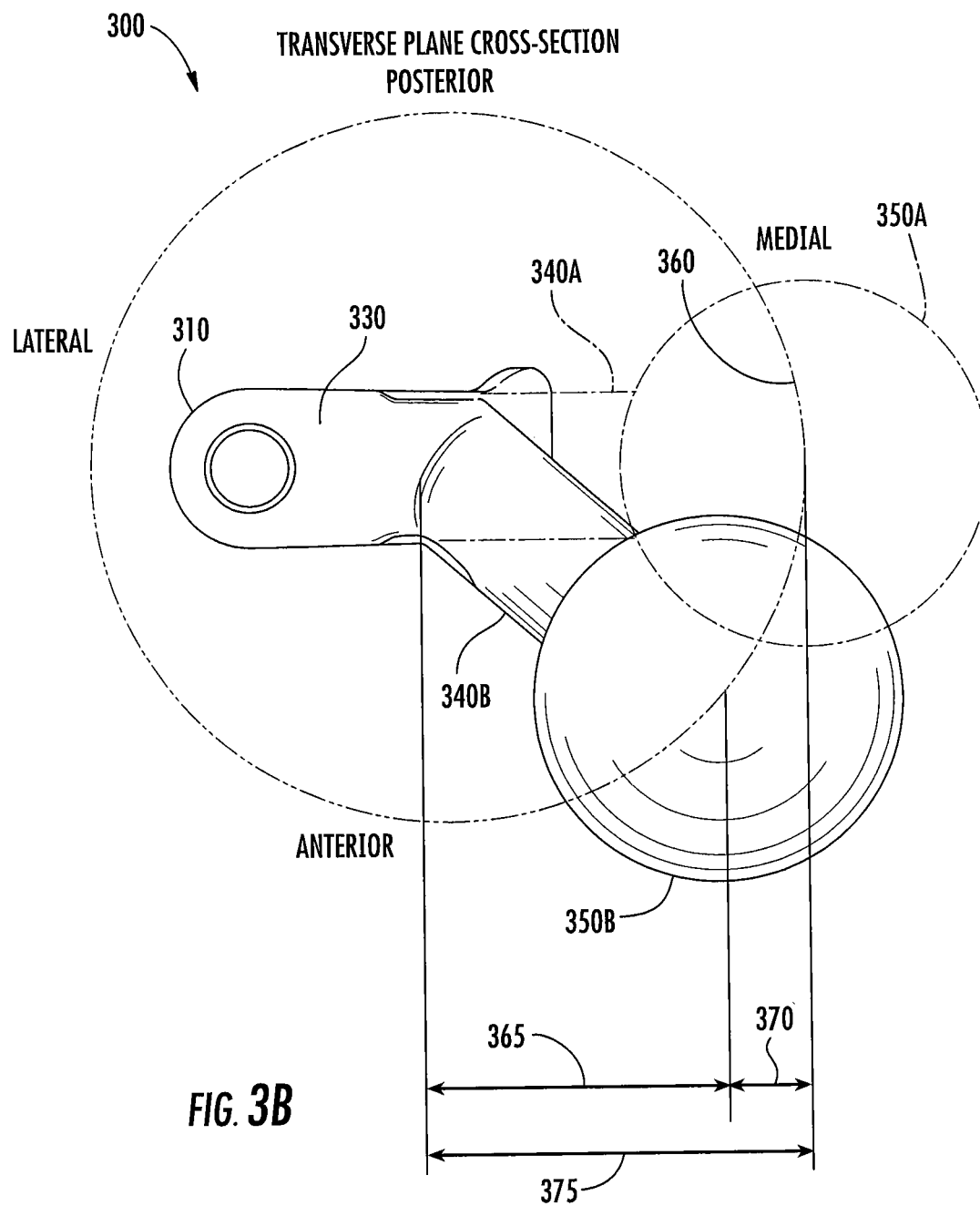
Figure 3C:
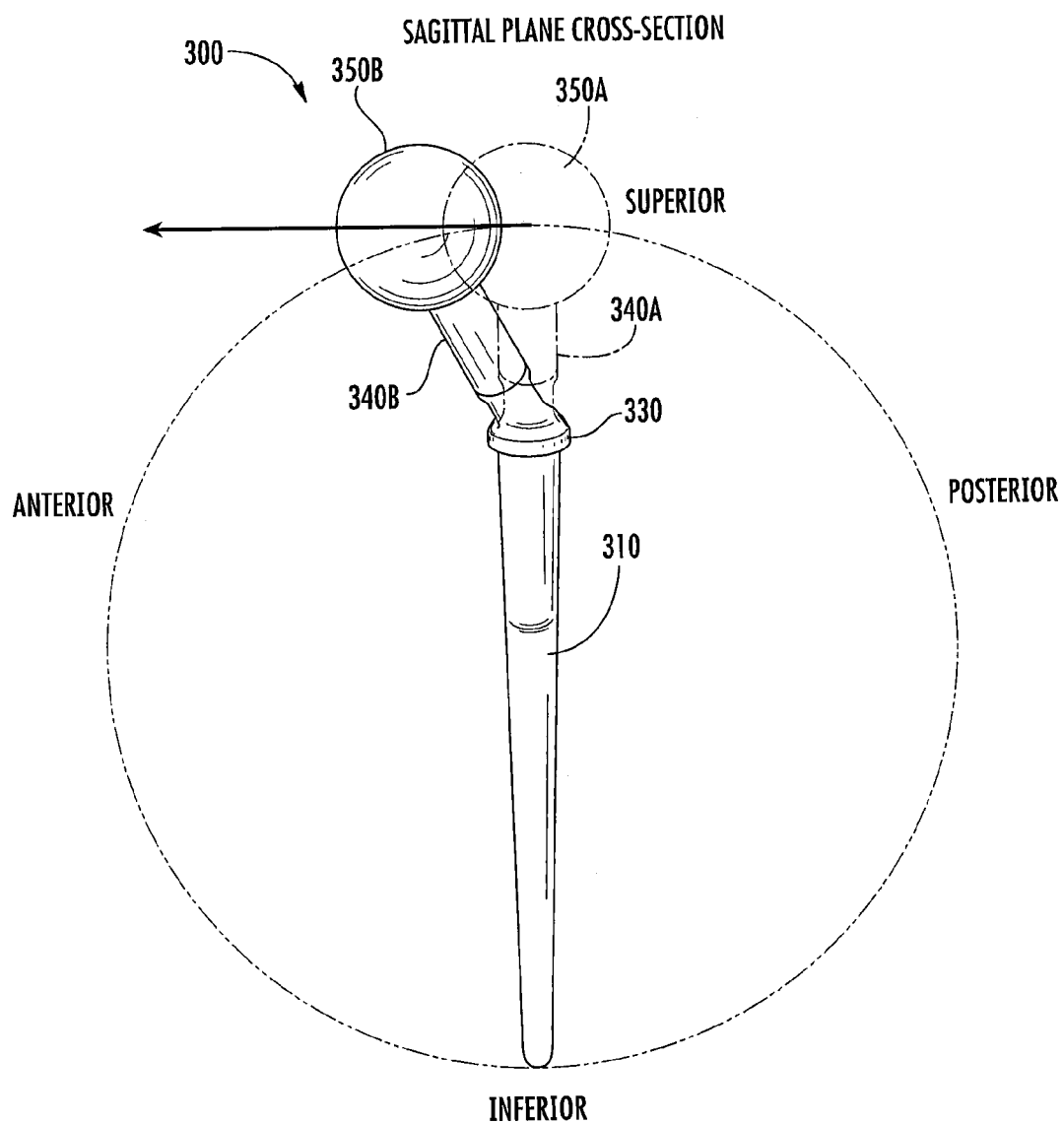
Figure 3D:
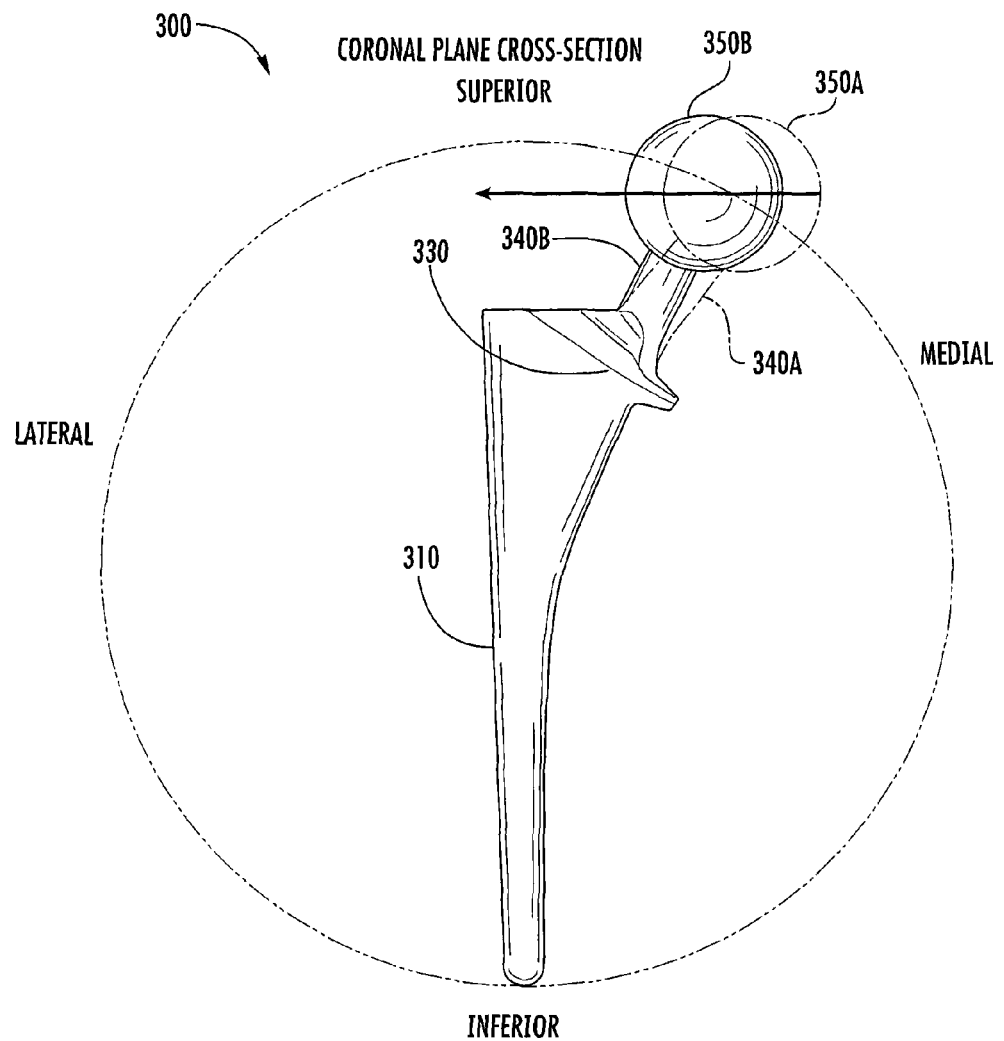
Figure 4A:
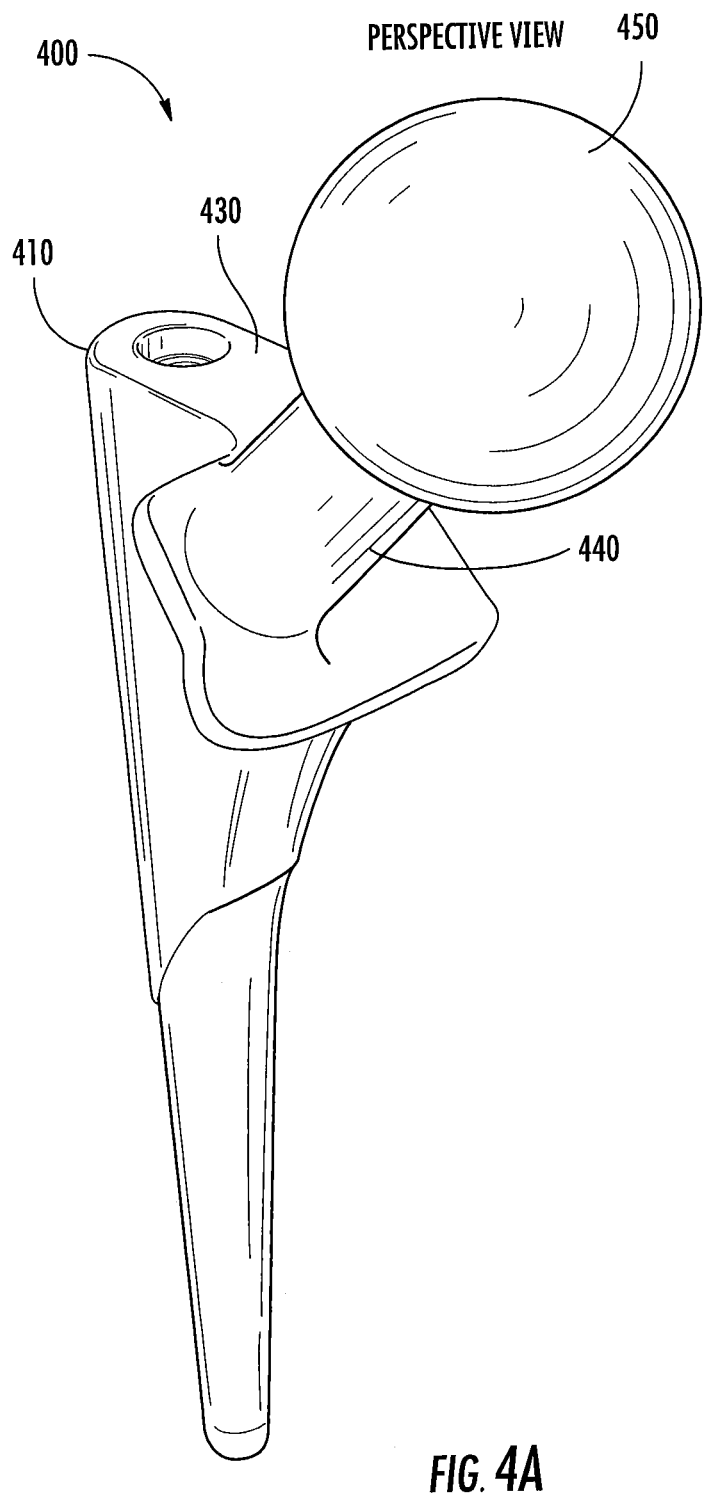
Figure 4B:
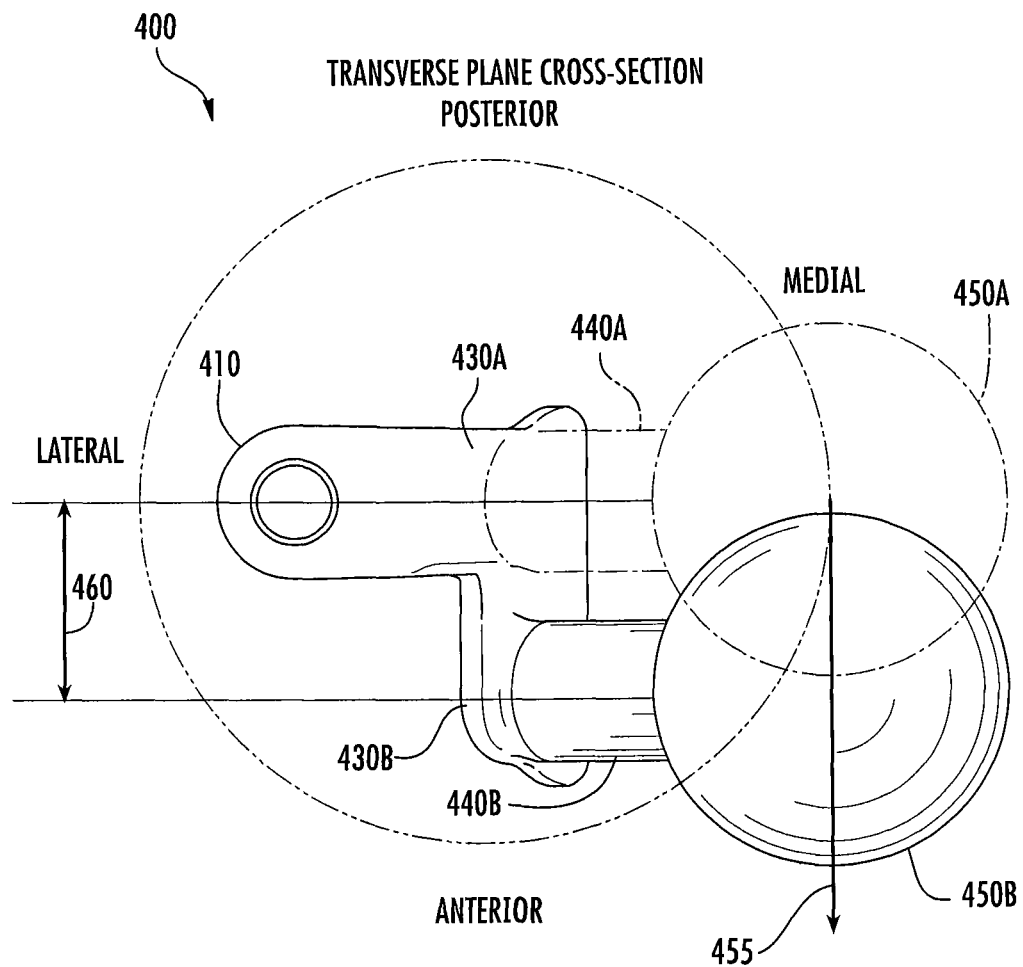
Figure 4C:
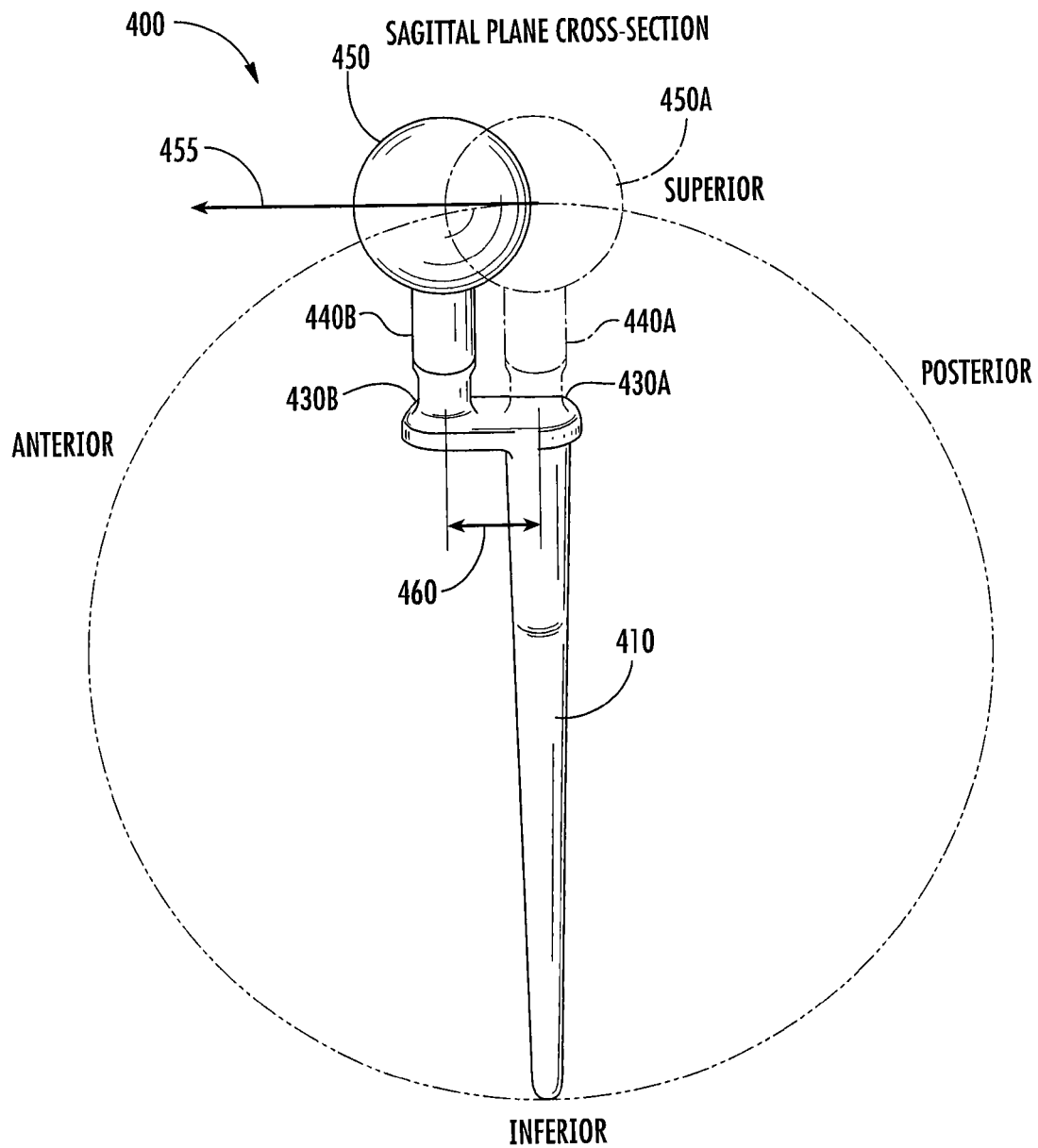
Figure 4D:
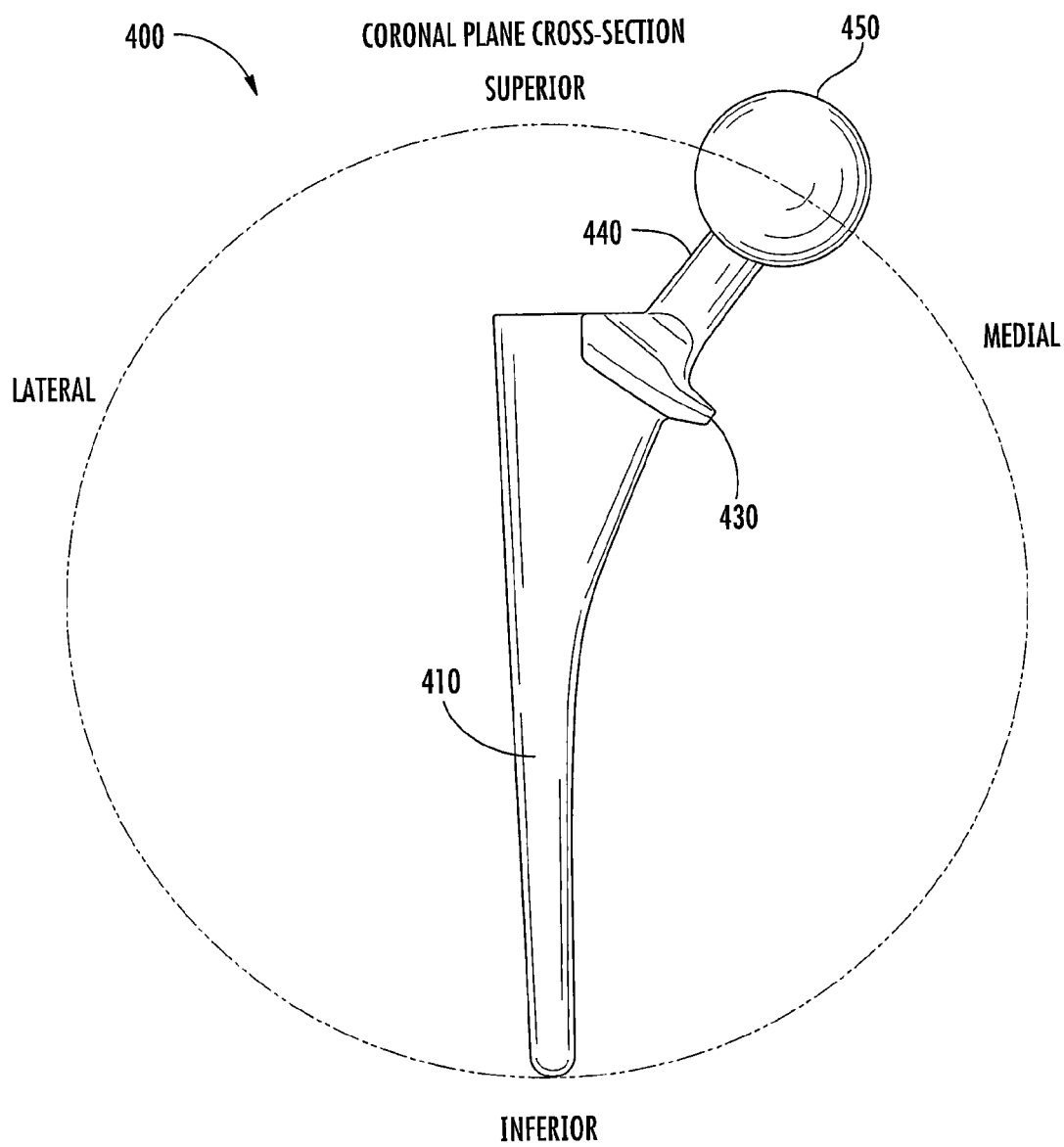
Figure 5A:
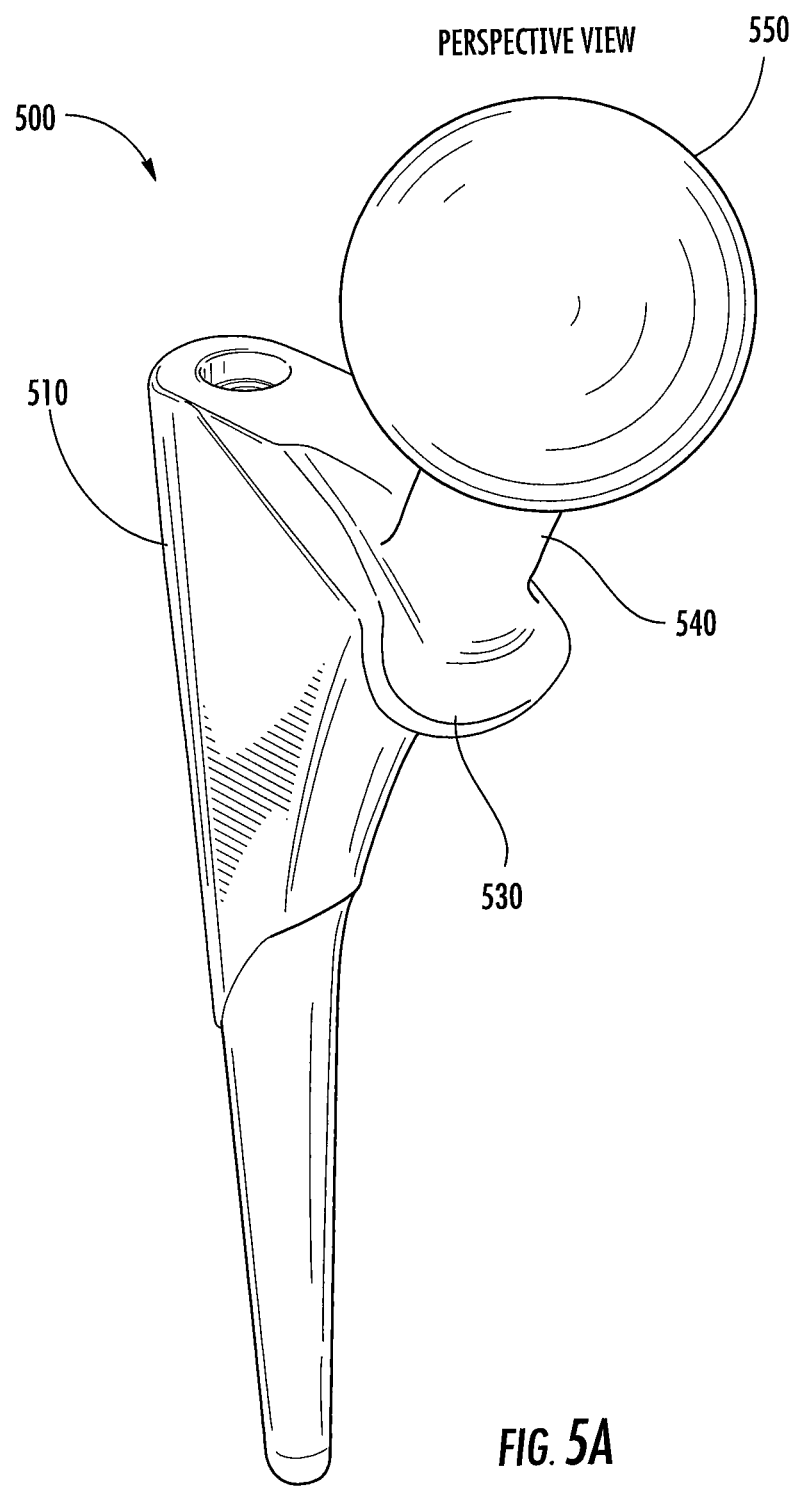
Figure 5B:
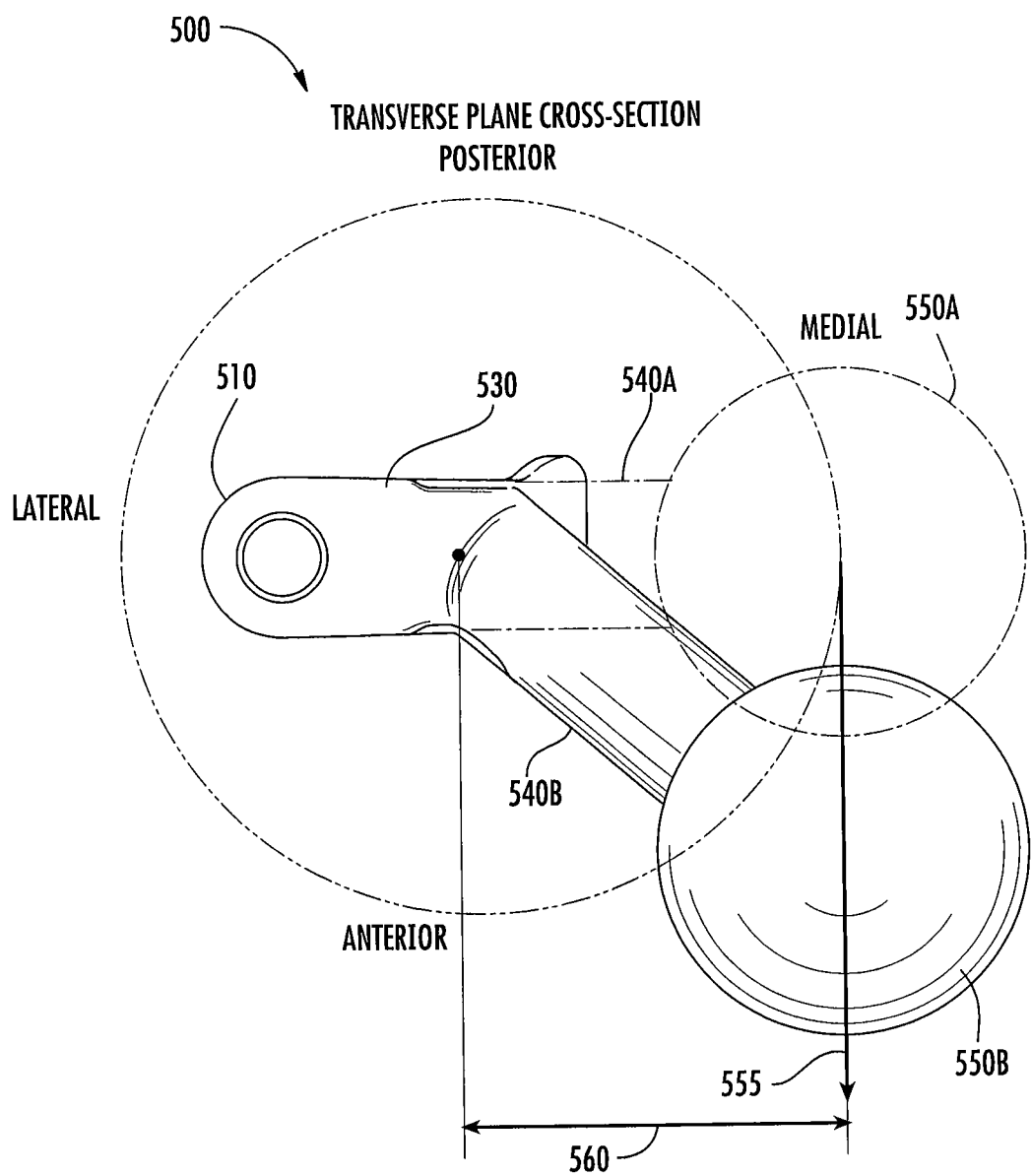
Figure 5C:
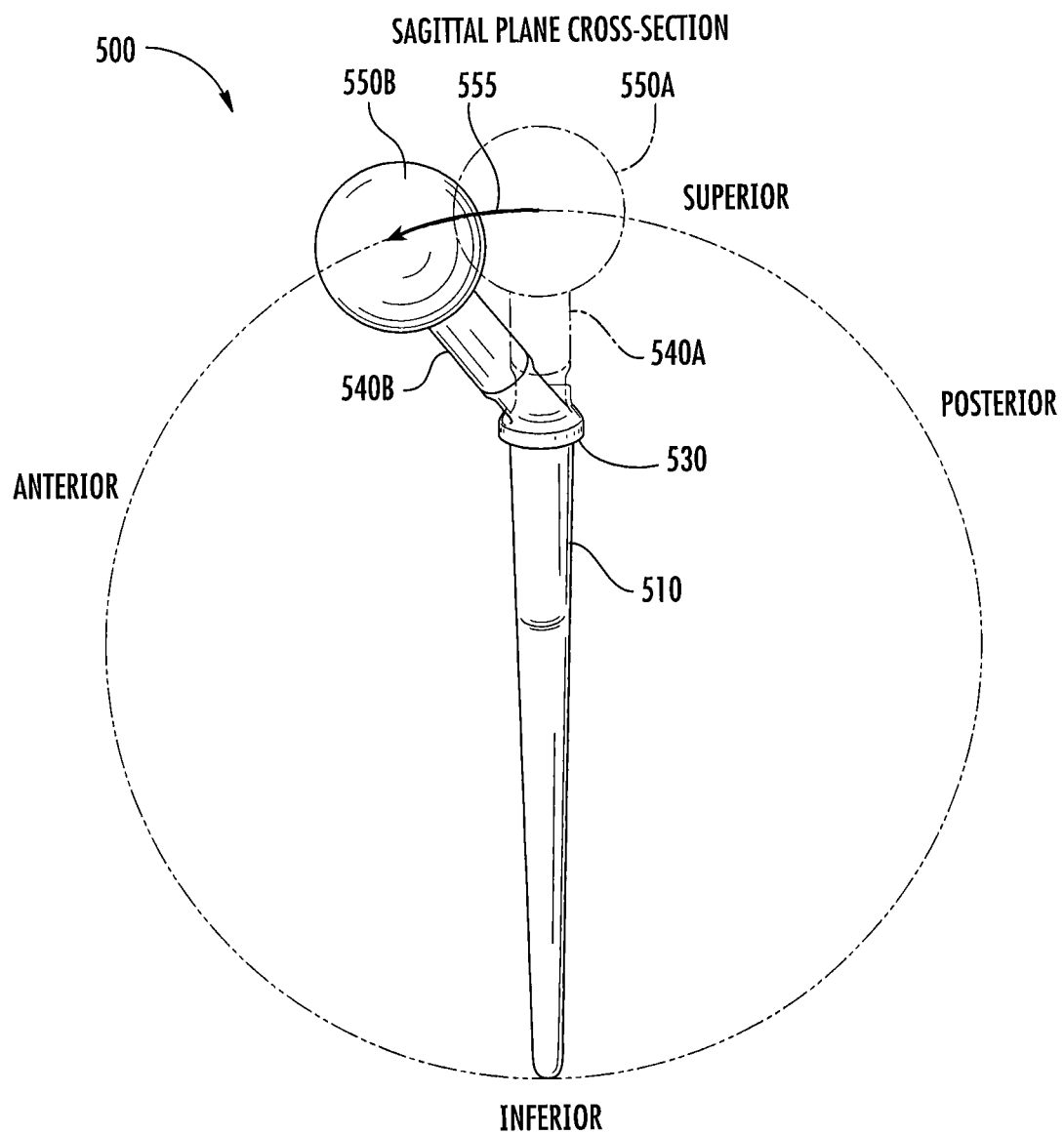
Figure 5D:
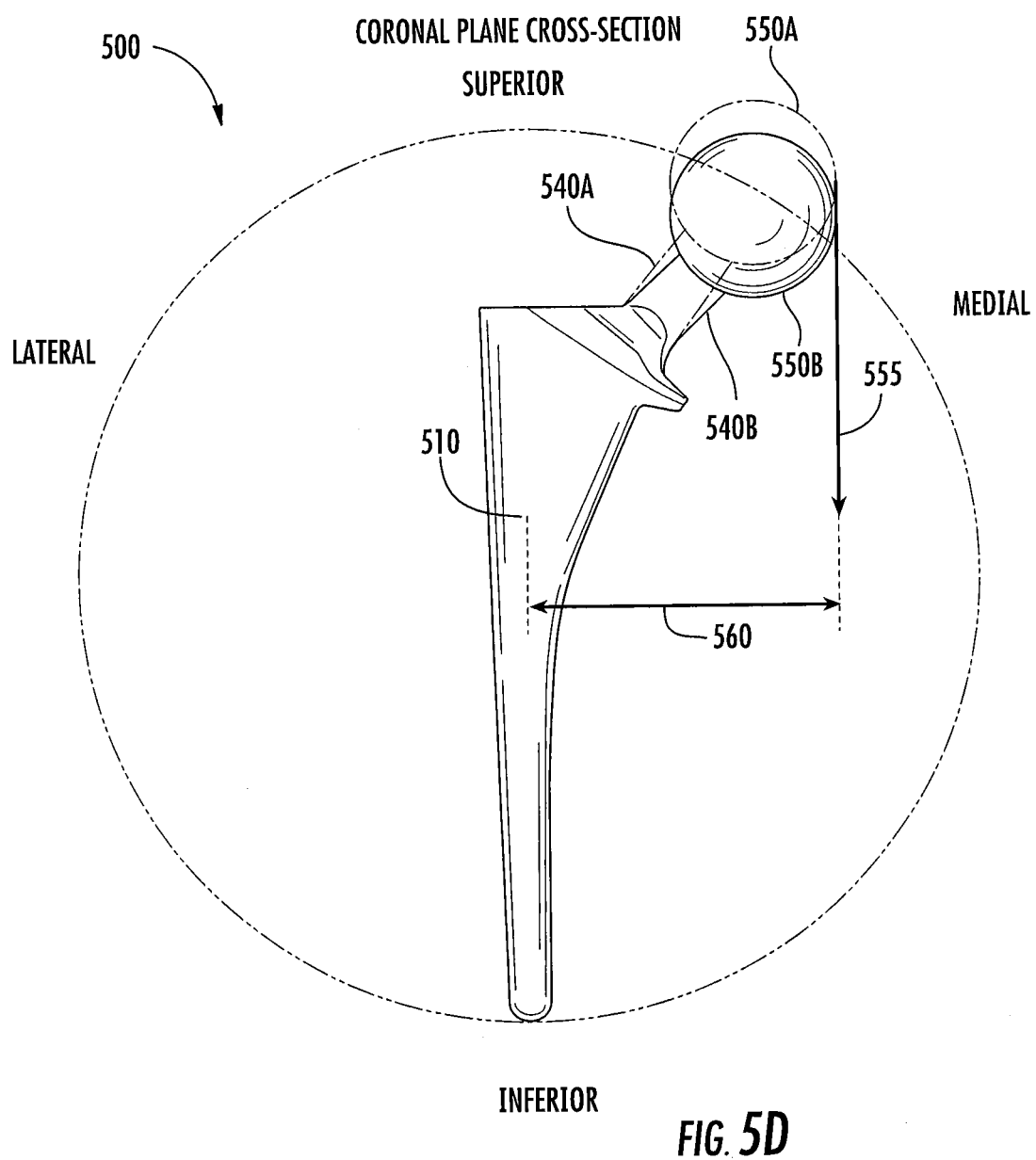
Figure 6A:
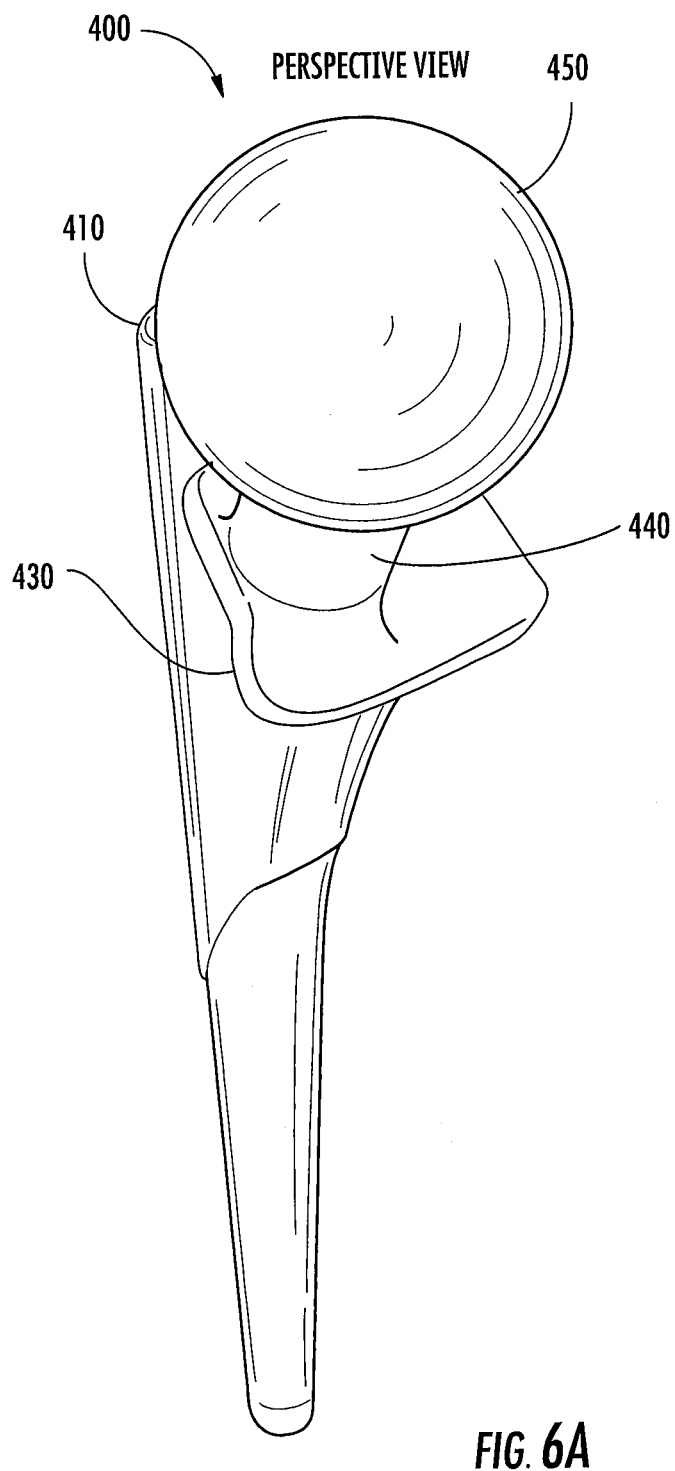
Figure 6B:
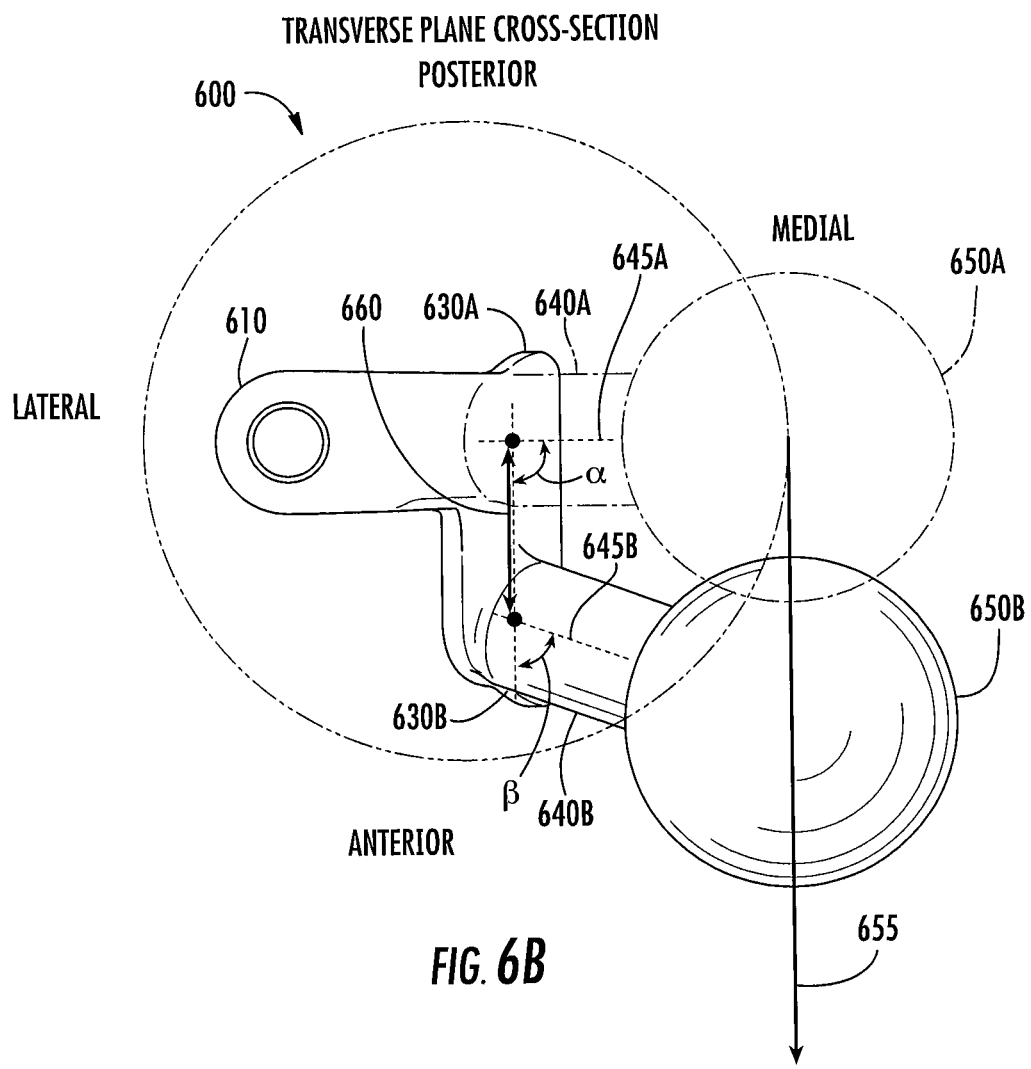
Figure 6C:
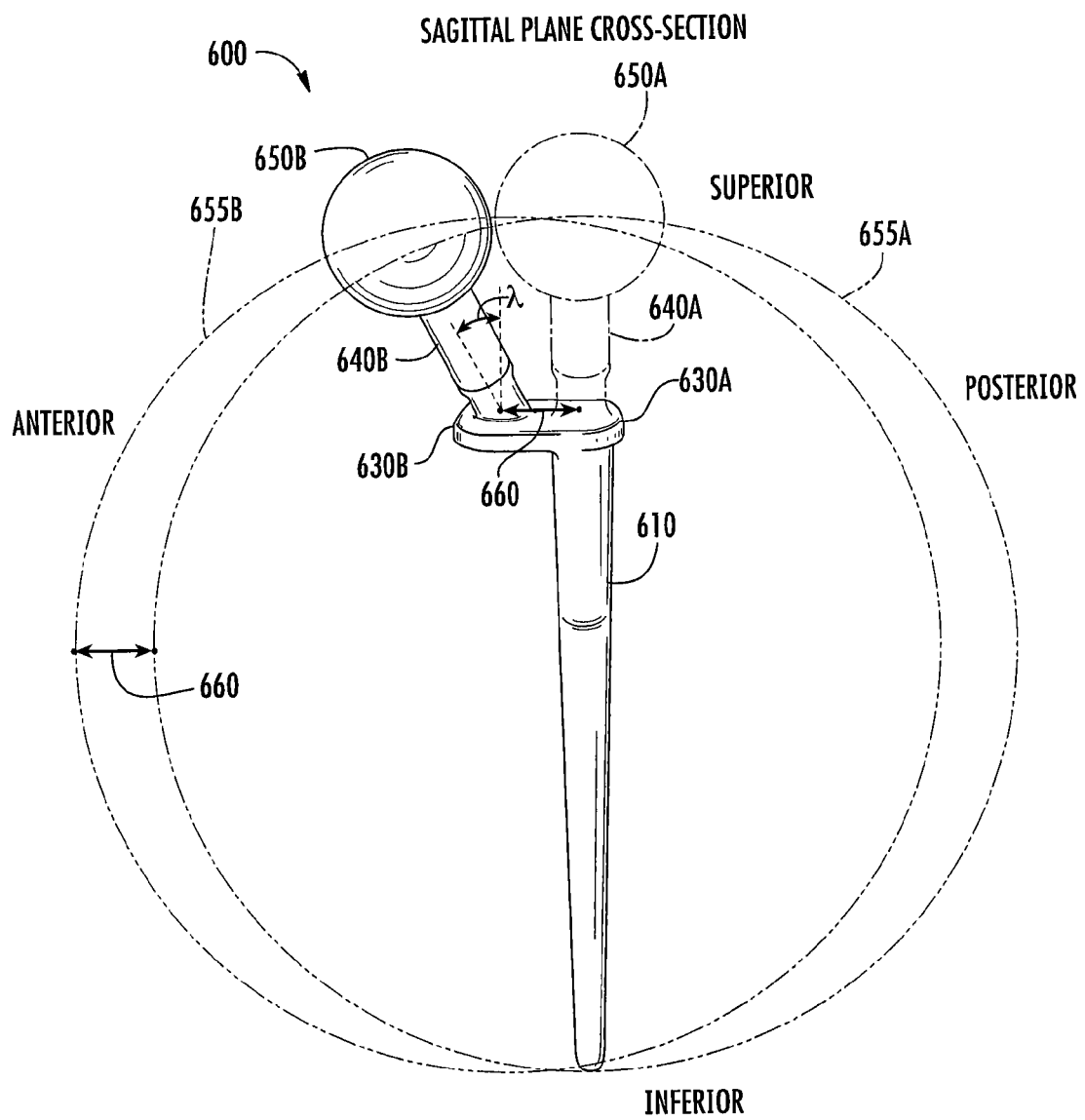
Figure 6D:
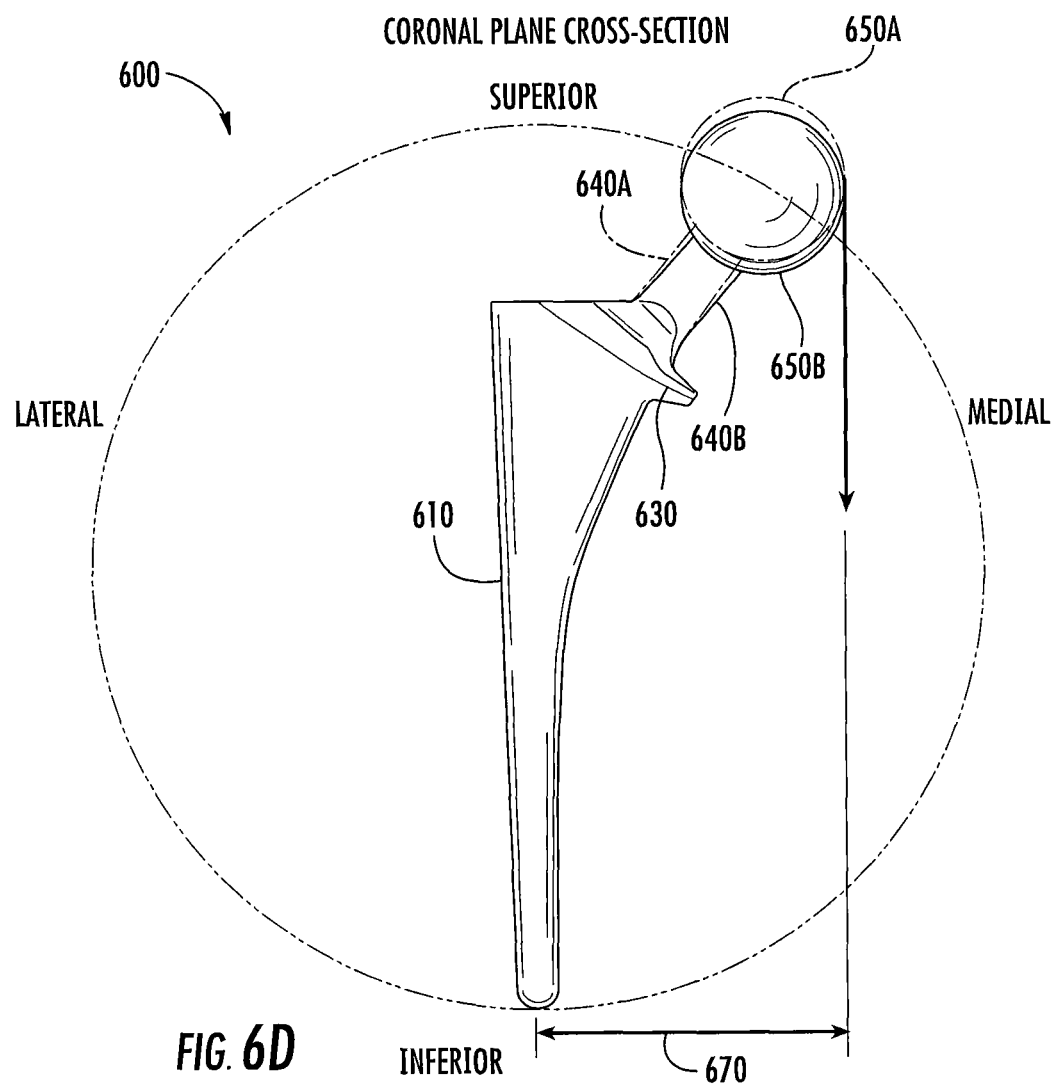

FIGS. 3B, 3C, and 3D are cross-sectional diagrams illustrating the femoral component of FIG. 3A for use in a hip replacement procedure in the transverse plane, the sagittal plane, and the coronal plane, respectively;

FIG. 4A is a perspective diagram illustrating a femoral component for use in a hip replacement procedure according to embodiments of the invention;

FIGS. 4B, 4C, and 4D are cross-sectional diagrams illustrating the femoral component of FIG. 4A for use in a hip replacement procedure in the transverse plane, the sagittal plane, and the coronal plane, respectively, according to embodiments of the invention;

FIG. 5A is a perspective diagram illustrating another femoral component for use in a hip replacement procedure according to embodiments of the invention;

FIGS. 5B, 5C, and 5D are cross-sectional diagrams illustrating the femoral component of FIG. 5A for use in a hip replacement procedure in the transverse plane, the sagittal plane, and the coronal plane, respectively, according to embodiments of the invention;

FIG. 6A is a perspective diagram illustrating another femoral component for use in a hip replacement procedure according to embodiments of the invention; and FIGS. 6B, 6C, and 6D are cross-sectional diagrams illustrating the femoral component of FIG. 6A for use in a hip replacement procedure in the transverse plane, the sagittal plane, and the coronal plane, respectively, according to embodiments of the invention.

DETAILED DESCRIPTION OF EMBODIMENTS OF THE INVENTION

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Embodiments of the invention provide a component configured for implantation during a total hip replacement procedure being performed on a patient. The component includes a stem configured for intraosseous femoral implantation. The stem has a distal end configured for femoral insertion and a proximal end opposite the distal end. The component has a neck attached to the stem at a neck-stem junction. The neck has a proximal end proximate the neck-stem junction and a distal end opposite the proximal end. The neck is configured for extraosseous implantation. The component also has a head attached to the neck proximate the distal end of the neck. The head (also referred to as the ball) is configured for coupling with a socket implanted in an acetabulum of a pelvis of the patient during the procedure, thereby forming a total hip replacement.

The invention provides anterior displacement of the head relative to the intraosseous stem, thereby minimizing instances of dislocation, while also minimizing instances of other negative outcomes. A first embodiment provides anterior displacement of the head relative to the stem by offsetting the neck and head relative to the stem proximate the junction of the stem and the neck. A second embodiment provides anterior displacement of the head relative to the stem by angulating, in the extraosseous portion of the component, the neck relative to the stem in the sagittal plane. A third embodiment provides anterior displacement of the head relative to the stem by both (1) offsetting the neck and head relative to the stem proximate the junction of the stem and the neck and (2) angulating, in the extraosseous portion of the component, the neck relative to the stem in the sagittal plane.

As discussed above, this anterior offset is configured to enhance both anterior and posterior stability of the replacement hip, and also reduces the risk of leg lengthening and/or shortening as compared with current component designs. The various embodiments of the invention retain an intraosseous stem which is straight in the sagittal plane in the femur proximate the hip of the patient, thereby retaining various benefits. However, all current designs utilizing anterior offset link anterior offset with medial-lateral offset of the head relative to the stem, thereby creating certain negative effects in many subjects. Negative effects may include in-toeing gait, diminution of abductor moment, frequent leg lengthening and others. The anterior offset of embodiments of the invention minimizes or eliminates such negative effects while reducing instability of the hip anteriorly and posteriorly, thereby reducing incidents of displacement of the hip.

Referring now to FIG. 1, a reference diagram illustrates a sagittal plane, a coronal plane, and a transverse plane of a representative patient. As shown, the sagittal plane is defined as a plane cutting the patient longitudinally or vertically from posterior to anterior. The coronal plane, as shown, is defined as a plane cutting the patient longitudinally or vertically from side to side. Finally, the transverse plane, as shown, is defined as cutting the patient latitudinally or horizontally.

Referring now to FIG. 2, a diagram illustrates a femoral component for use in a hip replacement procedure. The femoral component shown is an example of a type of femoral component used in total hip replacements, and is included here as a reference. The component 200 has a stem 210 for insertion and implantation inside a cavity longitudinally cleared in a proximal end of a patient's femur bone. The stem has a distal end 215 and a proximal end 220, which is attached to a neck 240 of the component 200 at a neck-stem junction or junction 230. Generally, the junction 230, neck 240 and head (not shown) remain outside the femur bone or extraosseous with regard to the femur. In some implementations, the proximal end 220 of the stem 210 includes some roughing 260 such that the tissue surrounding the component 200 will more effectively bond with the component, thereby producing a more stable implant and hip. The neck 240 supports and couples with a ball 250 configured for coupling with an acetabular cup or socket, thereby completing the total hip replacement.

Referring now to FIGS. 3A-3D diagrams illustrate a femoral component for use in a hip replacement procedure. FIG. 3A illustrates a perspective view, and FIGS. 3B, 3C, and 3D, are cross-sectional diagrams that illustrate the femoral component for use in a hip replacement procedure in the transverse plane, the sagittal plane, and the coronal plane, respectively. The components discussed with reference to FIGS. 3A-3D, have an anterior offset, however, these embodiments achieve the anterior offset by way of fixed or variable angle flexion of the neck relative to the stem (apex posterior), in the transverse plane. Flexion refers to angling with respect to a normal component, such as the component described above with reference to FIG. 2. Thus, any anterior displacement in the transverse plane is accomplished by an equal amount of lateral displacement in the transverse and coronal planes. Such lateral displacement diminishes the lever arm of the hip abductors and results in decreased abduction strength. In light of this, patients frequently respond to more than normal anteversion with its attendant weakness by walking pigeon-toed. Many find doing so objectionable cosmetically and functionally. In order to avoid unpleasant side effects of excessive anteversion, surgeons frequently accept normal or optimal anteversion but inadequate anterior displacement, thereby resulting in increased instability of the hip. This increased risk of instability is often offset by leg lengthening, which increases stability by increasing soft tissue tension, but is highly objectionable to patients.

Referring to FIG. 3A, component 300 has a stem 310 and a junction 330 connecting the stem 310 with neck 340. The neck 340 is coupled with head (or ball) 350.

Referring specifically to FIG. 3B, a cross-section of the component 300 taken in the transverse plane is shown. The component 300 has a stem 310 and a junction 330 connecting the stem 310 with neck 340A. The neck 340A is coupled with a ball 350A. As shown by arrow 360, in some implementations of the component 300, anterior offset is accomplished by way of creating a component by effectively flexing, i.e., rotating the neck, head and ball in the transverse plane, thereby resulting in a component 300 having neck 340B and ball 350B. In some implementations, the neck, head and ball actually rotate, such as in a modular component, and in other implementations, the neck, head and ball do not actually rotate, such as in the a modular component, but rather are fabricated such that the neck, head and ball represent a transverse angular difference from the normal component. Notably, the medial-lateral distance from the junction 330 to the ball 350A is represented by distance 375, whereas the medial-lateral distance from the junction 330 to the ball 350B is only distance 365, which is a distance 370 less than distance 375. This difference in medial-lateral distance, as discussed above, diminishes the lever arm of the hip abductors and results in decreased abduction strength, among other potential problems.

Referring specifically to FIG. 3C, a cross-section of the component 300 taken in the sagittal plane is shown. As shown, no difference in inferior-superior distance results from the anterior offset by anteversion. Referring specifically now to FIG. 3D, a cross-section of the component 300 taken in the coronal plane is shown. As shown, there is a lateral-medial difference between the neck 340A and ball 350A of the normal component and the neck 340B and ball 350B of the component having an anterior offset by anteversion.

Referring now to FIGS. 4B, 4C, and 4D, cross-sectional diagrams illustrate a femoral component for use in a hip replacement procedure in the transverse plane, the sagittal plane, and the coronal plane, respectively, according to embodiments of the invention. To achieve anterior offset of the component 400, the extraosseous neck and head are displaced anteriorly with respect to the intraosseous stem at the junction of the component. Thus, the neck and head may be displaced by a pure anterior offset without anteversion. These embodiments change the position of the neck and head relative to the stem in an anterior direction only.

Virtually all total hip dislocations occur either posteriorly or anteriorly. Furthermore, virtually all dislocations occur because the ball is levered out of the socket. The mechanism and fulcrum for the lever is different for posterior and anterior dislocations. Posterior dislocations occur when the hip is internally rotated. At the terminal point of internal rotation, the anterior edge of the greater trochanter contacts the flesh and bone of the pelvis. Further internal rotation levers the ball out of the socket and it displaces posteriorly. On the other hand, anterior dislocations occur when the hip is externally rotated. At the terminal point of external rotation, the prosthetic femoral neck contacts the posterior edge of the cup or socket, which may either be prosthetic or natural depending on prosthetic cup placement. Further external rotation levers the ball out of the socket and it displaces anteriorly.

When a straight stem is placed in the femoral canal, the direction in the sagittal plane of the proximal native femoral shaft results in the base of the neck of the prosthesis being posterior to the native neck. If the version of the neck relative to the stem is then reproduced, this results in the prosthetic head being posteriorly displaced relative to the native head. This results in the leading edge of the greater trochanter being relatively anterior to the head, which means that it contacts the pelvis earlier in internal rotation than it would otherwise, and therefore dislocates posteriorly with less internal rotation. Likewise, because the prosthetic head is displaced posteriorly compared to the anatomic head and neck, contact of the prosthetic neck and cup occurs earlier with external rotation, and therefore anterior dislocation occurs with less external rotation. Offsetting the prosthetic head and neck anteriorly enhances both posterior stability, by moving the anterior edge of the greater trochanter posterior relative to the head, and anterior stability, by moving the prosthetic neck further away from the cup, delaying impingement and anterior dislocation.

Referring now to FIGS. 4A-4D diagrams illustrate a femoral component for use in a hip replacement procedure according to embodiments of the invention. FIG. 4A illustrates a perspective view, and FIGS. 4B, 4C, and 4D, are cross-sectional diagrams of the femoral component for use in a hip replacement procedure in the transverse plane, the sagittal plane, and the coronal plane, respectively.

Referring to FIG. 4A, component 400 has a stem 410 and a junction 430 connecting the stem 410 with neck 440. The neck 440 is coupled with head (or ball) 450.

Referring collectively to FIGS. 4A-4D, a normal component 400 has a stem 410, a junction 430A a neck 440A and a ball 450A. As shown, embodiments of the invention provide for displacing the neck 440B and ball 450B in the direction of arrow 455 a posterior-anterior distance 460. The base of the neck proximate the junction 430B is offset the same or nearly the same distance as the end of the neck proximate the ball 450B.

The neck, head and ball may also be displaced anterior to the stem by flexing or rotating the neck, head and ball in the sagittal plane (apex posterior) at the neck-stem junction during fabrication of the component. This rotation produces anterior displacement in the sagittal and transverse planes equal to the inferior displacement in the sagittal and coronal planes.

Referring now to FIGS. 5A-5D diagrams illustrate a femoral component for use in a hip replacement procedure according to embodiments of the invention. FIG. 5A illustrates a perspective view, and FIGS. 5B, 5C, and 5D, are cross-sectional diagrams that illustrate the femoral component for use in a hip replacement procedure in the transverse plane, the sagittal plane, and the coronal plane, respectively.

Referring to FIG. 5A, component 500 has a stem 510 and a junction 530 connecting the stem 510 with neck 540. The neck 540 is coupled with head (or ball) 550.

Referring collectively to FIGS. 5B-5D, cross-sectional diagrams illustrate the femoral component for use in a hip replacement procedure in the transverse plane, the sagittal plane, and the coronal plane, respectively, according to embodiments of the invention. The normal component 500 has a stem 510, a junction 530, a neck 540A and a ball 550A. The neck 540B, head and ball 550B is rotated in the direction of arrow 555 at the junction 530 to provide anterior offset. As indicated above, the term rotation merely refers to the location of the neck 540B with respect to where the normal neck 540A would be fabricated. Notably, as shown in FIG. 5A, the medial-lateral distance 560 remains the same in the component 400 having an angled neck 540B. However, the inferior-superior distance diminishes as shown in FIG. 5C.

The neck and head may also be displaced anterior to the stem by a combination of anterior offset and flexing or rotating, either via fabrication or via modular component, the neck and head in the sagittal plane.

Referring now to FIGS. 6A-6D diagrams illustrate a femoral component for use in a hip replacement procedure. FIG. 6A illustrates a perspective view, and FIGS. 6B-6D, cross-sectional diagrams illustrate the femoral component for use in a hip replacement procedure in the transverse plane, the sagittal plane, and the coronal plane, respectively.

Referring to FIG. 6A, component 600 has a stem 610 and a junction 630 connecting the stem 610 with neck 640. The neck 640 is coupled with head (or ball) 650.

Referring now to FIGS. 6B, 6C, and 6D, cross-sectional diagrams illustrate the femoral component for use in a hip replacement procedure in the transverse plane, the sagittal plane, and the coronal plane, respectively, according to embodiments of the invention. The normal component 600 has a stem 610, a junction 630A, a stem 640A, and a ball 650A. The component has an anteriorly offset junction 630B displaced a distance 660 as well as a sagittal plane angulation. As shown, angle $\alpha$ is greater than angle $\beta$ indicating that neck 640 and ball 650B have been positioned or rotated in the direction of arrow 655 an angle $\gamma$. As shown in FIG. 6B, the neck 640B and ball 650B are positioned or rotated in the direction of arrow 655B. Referring to FIG. 6C, the lateral-medial distance 670 does not change.

Pure anterior offset, as discussed with reference to FIGS. 4A-4D, may be limited in the amount of change potentially achieved because the offset decreases contact between the head and neck as well as the stem in the sagittal plane by the amount it is offset. Flexion of the component at the junction in the sagittal plane permits greater anterior displacement of the head/ball relative to the stem without compromising the strength of the component at the junction.

In summary, embodiments of the invention provide a component configured for implantation during a total hip replacement procedure being performed on a patient. The component includes a stem configured for intraosseous femoral implantation. The stem has a distal end configured for femoral insertion and a proximal end opposite the distal end. The component has a neck attached to the stem at a neck-stem junction. The neck has a proximal end proximate the neck-stem junction and a distal end opposite the proximal end. The neck is configured for extraosseous implantation. The component also has a head attached to the neck proximate the distal end of the neck. The head is configured for coupling with a ball configured for coupling with a socket implanted in an acetabulum of a pelvis of the patient during the procedure, thereby forming a total hip replacement. The head is anteriorly offset relative to the stem.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other updates, combinations, omissions, modifications and substitutions, in addition to those set forth in the above paragraphs, are possible. Those skilled in the art may appreciate that various adaptations and modifications of the just described embodiments can be configured without departing from the scope and spirit of the invention. Therefore, it is to be understood that, within the scope of the appended claims, the invention may be practiced other than as specifically described herein.

The invention claimed is:

1. A component configured for implantation during a total hip replacement procedure being performed on a patient, the patient having an anterior and posterior and defining a sagittal plane, a transverse plane and a coronal plane, the component comprising:
   a stem configured for intraosseous femoral implantation, the stem having a distal end configured for femoral insertion and a proximal end opposite the distal end;
   a neck-stem junction platform comprising a neck portion and a stem portion opposite the neck portion, the stem portion connected with the proximal end of the stem at a stem connection point, the neck-stem junction platform configured for extraosseous femoral implantation without any intraosseous implantation, wherein the neck portion and the stem portion form an L-shaped platform;
   a neck attached to the stem by the neck-stem junction platform, the neck having a proximal end connected with the neck portion of the neck-stem junction platform at a neck connection point and a distal end opposite the proximal end, the neck configured for extraosseous femoral implantation;
   wherein the stem portion of the neck-stem junction platform defines a lateral-medial axis through the stem connection point and the neck portion of the neck-stem junction platform defines a posterior-anterior axis through the neck connection point, the lateral medial axis and the posterior-anterior axis intersecting at an intersection point and being substantially perpendicular to each other;
   wherein the stem connection point is a lateral-medial distance parallel to the lateral-medial axis from the intersection point; and
   wherein the stem connection point is a posterior-anterior distance parallel to the posterior-anterior axis from the intersection point; and
   a head attached to the neck proximate the distal end of the neck, the head configured for coupling with a socket implanted in an acetabulum of a pelvis of the patient during the procedure, thereby forming a total hip replacement.

2. The component of claim 1, wherein all of the neck is anteriorly offset with respect to the stem.

3. The component of claim 1, wherein the proximal end of the neck and the distal end of the neck are anteriorly offset relative to the stem substantially the same amount.

4. A total hip replacement system for implantation during a total hip replacement procedure being performed on a patient, the patient having an anterior and posterior and defining a sagittal plane, a transverse plane and a coronal plane, the system comprising:
   a socket component configured for implantation in an acetabulum of a pelvis of the patient during the procedure; and
   a femoral component configured for implantation in a femur of the patient and configured for coupling with the socket component, the femoral component comprising:
      a stem configured for intraosseous femoral implantation, the stem having a distal end configured for femoral insertion and a proximal end opposite the distal end;
      a neck-stem junction platform comprising a neck portion and a stem portion opposite the neck portion, the stem portion connected with the proximal end of the stem at a stem connection point, the neck-stem junction platform configured for extraosseous femoral implantation without any intraosseous implantation, wherein the neck portion and the stem portion form an L-shaped platform;
      a neck attached to the stem by the neck-stem junction platform, the neck having a proximal end connected with the neck portion of the neck-stem junction platform at a neck connection point and a distal end opposite the proximal end, the neck configured for extraosseous femoral implantation;
      wherein the stem portion of the neck-stem junction platform defines a lateral-medial axis through the stem connection point and the neck portion of the neck-stem junction platform defines a posterior-anterior axis through the neck connection point, the lateral medial axis and the posterior-anterior axis intersecting at an intersection point and being substantially perpendicular to each other;
      wherein the stem connection point is a lateral-medial distance parallel to the lateral-medial axis from the intersection point; and
      wherein the stem connection point is a posterior-anterior distance parallel to the posterior-anterior axis from the intersection point; and
      a head attached to the neck proximate the distal end of the neck, the head configured for coupling with the socket component, thereby forming a total hip replacement.

5. The total hip replacement system of claim 4, wherein the neck is angled with respect to the stem in the sagittal plane of the patient, thereby further anteriorly offsetting the head relative to the stem.

6. The total hip replacement system of claim 4 wherein all of the neck is anteriorly offset with respect to the stem.

7. The total hip replacement system of claim 4, wherein the proximal end of the neck and the distal end of the neck are anteriorly offset relative to the stem substantially the same amount.

\* \* \* \* \*